(12) United States Patent
Alley

(10) Patent No.: US 6,513,673 B2
(45) Date of Patent: Feb. 4, 2003

(54) MULTIPLE-COMPARTMENT BIOLOGICAL SPECIMEN CASSETTE

(76) Inventor: Kenneth A. Alley, 311 Foundryville, Berwick, PA (US) 18603

( * ) Notice: Subject to any disclaimer, the term of this patent is extended or adjusted under 35 U.S.C. 154(b) by 0 days.

(21) Appl. No.: 10/139,471

(22) Filed: May 3, 2002

(65) Prior Publication Data

US 2002/0162843 A1 Nov. 7, 2002

Related U.S. Application Data

(60) Provisional application No. 60/288,668, filed on May 4, 2001.

(51) Int. Cl.$^7$ .............................................. B65D 81/00
(52) U.S. Cl. ..................... 220/524; 220/367.1; 220/523
(58) Field of Search ................................ 220/524, 523, 220/367.1, 607, 4.22, 4.24

(56) References Cited

U.S. PATENT DOCUMENTS

| | | | |
|---|---|---|---|
| 4,034,884 A | | 7/1977 | White ............................ 220/8 |
| 4,220,252 A | | 9/1980 | Beall et al. ................. 220/307 |
| 4,267,939 A | * | 5/1981 | Perrett et al. ......... 220/367.1 X |
| 4,421,246 A | | 12/1983 | Schultz et al. .............. 220/307 |
| 4,549,670 A | | 10/1985 | Trendler ...................... 220/338 |
| 4,798,292 A | * | 1/1989 | Hauze ................. 220/367.1 X |
| 5,127,537 A | | 7/1992 | Graham ....................... 220/339 |
| 5,533,642 A | | 7/1996 | Lafond et al. .............. 220/326 |
| 5,950,834 A | * | 9/1999 | Woodnorth et al. ..... 220/523 X |

* cited by examiner

Primary Examiner—Steven Pollard

(57) ABSTRACT

A multi-compartment biological specimen cassette. The perforations in one compartment of the cassette may have a different size and/or shape than the perforations in the other compartment or compartments.

12 Claims, 2 Drawing Sheets

MULTIPLE-COMPARTMENT BIOLOGICAL SPECIMEN CASSETTE

CROSS REFERENCE TO PRIORITY APPLICATION

This application claims the benefit of priority under all applicable statutes to U.S. Provisional Patent Application No. 60/288,668 filed May 4, 2001.

FIELD OF THE INVENTION

This invention relates to specimen or tissue cassettes and, more particularly, to a multi-compartment tissue cassette suitable for holding two (or more) samples simultaneously in their own respective compartments.

BRIEF DESCRIPTION OF THE PRIOR ART

Thin tissue samples taken during biopsies are commonly stored in small plastic containers or cassettes. These cassettes are used to hold the tissue samples during processing, until the samples are removed for testing or examining.

It is common for the cassettes to be placed in a histological tissue processing chamber. The chamber is designed to heat the tissue sample, and expose the sample to various chemical treatments (e.g., alcohols, xylene and formaldehydes) in order to preserve the sample. The sample is then embedded in paraffin wax in the cassette. The embedded samples are then removed from the cassettes, so that they can be sliced into thin sections for subsequent examination.

Tissue cassettes are well-known in the art; see for example, U.S. Pat. Nos. 4,034,884; 4,220,252; 4,421,246; 4,549,670; 5,127,537; and 5,533,642. Some of the first cassettes were manufactured from steel. Today, most cassettes are molded from plastics.

SUMMARY OF THE INVENTION

The present invention is a multi-compartmented tissue cassette. In the preferred embodiment, there are two compartments, one smaller than the other. The subject tissue cassette can hold a relatively small sample in the smaller of the two compartments and a larger sample in the larger of the two compartments. The two samples are physically isolated from each other but can be treated simultaneously. Also, in a preferred embodiment the perforations associated with the smaller compartment may be of different dimensions depending on the size of the tissue samples to be held in the various compartments.

BRIEF DESCRIPTION OF THE DRAWINGS

The foregoing summary, as well as the following detailed description may be better understood when read in conjunction with the accompanying drawings, which are incorporated in and form a part of the specification. The drawings serve to explain the principles of the invention and illustrate embodiments of the present invention that are preferred at the time the application was filed. It should be understood, however, that the invention is not limited to the precise arrangements and instrumentalities shown.

In the drawings.

DETAILED DESCRIPTION OF THE PREFERRED EMBODIMENT

Figure 1:
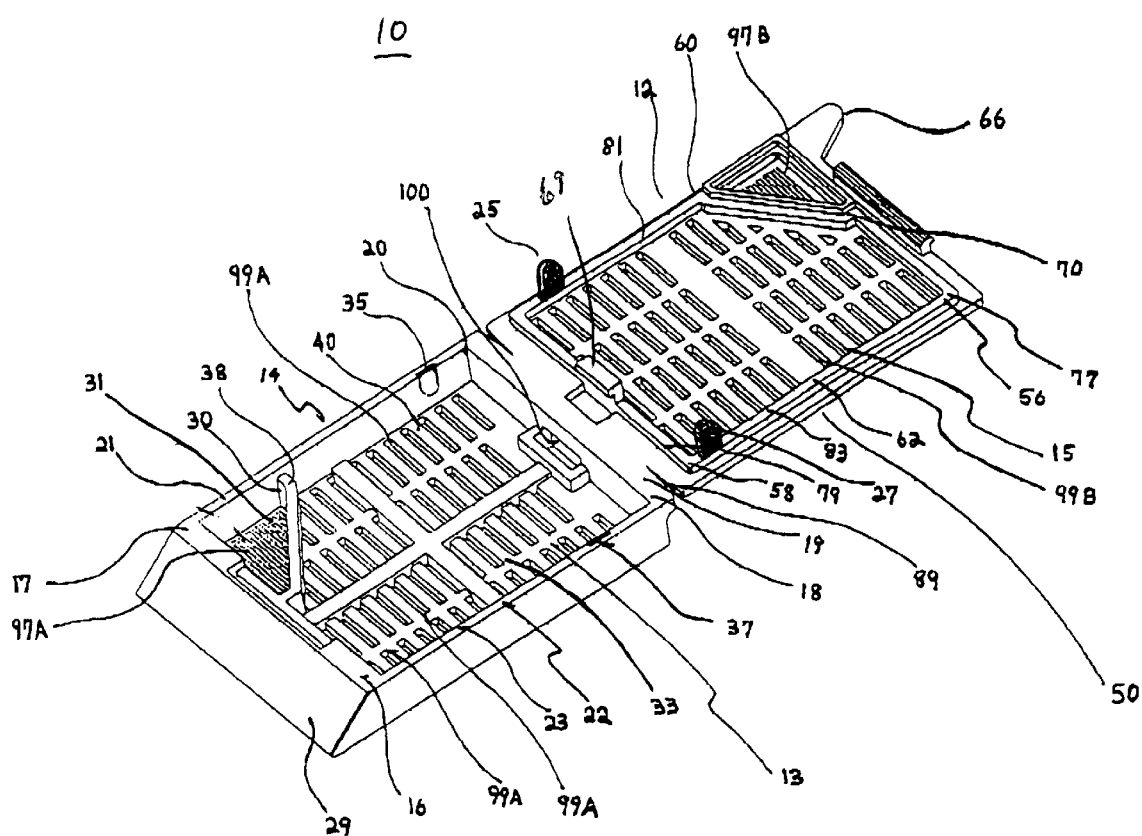
FIG. 1 is a top perspective view of a tissue cassette in accordance with the principles of the present invention.

In describing a preferred embodiment of the invention, specific terminology will be selected for the sake of clarity. However, the invention is not intended to be limited to the specific terms so selected, and it is to be understood that each specific term includes all technical equivalents that operate in a similar manner to accomplish a similar purpose.

The terms "right", "left", "top", "bottom", "lower" and "upper" designate relative directions in the drawings to which reference is made. The terms "inward" and "outward" will usually refer to an area or volume inside or outside, respectively, of the storage compartment of the subject tissue cassette.

The preferred embodiments of the present invention will now be described in detail with reference to the accompanying drawings in which a novel biological tissue cassette in accordance with the present invention is generally indicated at 10.

Referring to FIG. 1, the biological tissue cassette 10 includes a cover member 12 connected to a base member 14 via a living hinge 89. The cover and base members 12, 14 are substantially rectangular in shape. Although the shape of the cassette is not critical to the present invention, a rectangular shape allows the subject biological tissue cassette 10 to be stacked into standardized or existing equipment for later processing.

Background information, especially regarding the processing of tissue samples and the manufacturing of cassettes, is described in U.S. Pat. No. 4,220,252, issued Sep. 2, 1980 to Beall et al., and U.S. Pat. No. 5,127,537, issued Jul. 7, 1992, to Graham. U.S. Pat. No. 4,220,252 and U.S. Pat. No. 5,127,537 are hereby incorporated by reference as if both documents are fully set forth herein.

The base 14 has a generally flat bottom member 40, opposing parallel first and second endwalls 16, 18, depending upward along the traverse side of the bottom member 40, and opposing parallel third and fourth endwalls 20, 22 depending upward along the longitudinal sides of the bottom member 40. The endwalls 16, 18, 20, and 22 are joined at their respective ends and define a primary well or compartment 13 within base 14.

Also, a lower compartment wall 30 depends upward from the bottom member 40 at a predetermined position on the bottom member 14. As illustrated in FIG. 1, the compartment wall 30 has three segments and, along with a portion of endwalls 16, 20, defines a secondary well or compartment 31.

The shape of the compartment wall 30 is generally not important; however, it preferably starts at one endwall and ends at another endwall, and generally divides the base member 40 into two preferably unequally-sized compartments 13, 31. Although secondary compartment 31 is shown in the left front corner of the bottom member 40, it would be understood that the compartment wall 30 could define a compartment virtually anywhere in the primary compartment 13—even independent of any of the endwalls.

Endwalls 16, 18, 20, 22 and compartment wall 30 have coplanar upper edge surfaces 17, 19, 21, 23 and 38, respectively. After reading the present disclosure, it would be understood by one skilled in the art to manufacture a bottom member 14 having multiple compartment walls if more than two compartments are needed. Also, the location and/or shape of the second compartment (third compartment, fourth compartment, etc.) may be modified to suit a particular purpose.

The base member 40 has a plurality of first perforations 99A in the area directly corresponding to the primary compartment 13, and a plurality of second perforations 97A in the area directly corresponding of the secondary compartment 31. These perforations 97A, 99A allow chemicals to enter the interior of the cassette in order to treat the tissue sample stored inside the cassette 10. The perforations 97A, 99A also permit paraffin wax to pour into the cassette thereby encasing the sample. After reading the present disclosure, it would be understood by one skilled in the art that the size, shape and location of the perforations may be modified to accommodate a particular chemical or allow other liquids to pour into each compartment. Although the drawings indicate that second perforations 97A are smaller in dimension than perforations 99A, it may not necessarily be true that the smaller, secondary compartment 31 has smaller perforations 97A. Moreover, each compartment may have more than one size or shape of perforations.

The cover 12 has a generally flat top member 50, opposing parallel first and second endwalls 56, 58, depending downward from the top sheet along its traverse side, and opposing parallel third and fourth endwalls 60, 62 depending downward along the longitudinal sides of the top member 50. The endwalls 56, 58, 60, and 62 define an upper primary compartment 15 within cover 12. Endwalls 56, 58, 60, 62 have coplanar lower edge surfaces 77, 79, 81, 83, respectively.

Ears 25, 27 depend downward from upper endwalls 60, 62, respectively. Detents 35, 37 in the lower endwalls 20, 22 are aligned with ears 25, 27, respectively, when the member 12 is closed over the bottom member 14. The ear/detent arrangement helps to secure and align the top member 12 to the bottom member 14.

The endwalls 56, 58, 60, and 62 of the cover 12 are slightly shorter in length than, and usually not as deep as, endwalls 16, 18, 20, and 22 of base 14; this allows the endwalls 56, 58, 60, 62 of the cover 12 to frictionally fit inside the endwalls 16, 18, 20, 22 of the base member 14. (Although not necessary, the length and width of cover 12 may also be slightly less than the length and width of base 14.)

An upper compartment wall 70 depends downward from the cover 12 at a pre-determined position corresponding exactly with the lower compartment wall 30 on the base 14. The upper compartment wall 70 defines secondary upper compartment 51 on cover 12. Similar to the lower compartment wall 30, the shape of the upper compartment wall 70 is generally not important as long as it mirrors the lower compartment wall 30. The depth of upper compartment wall 70 is at least equal to the depth of endwalls 56, 58, 60, 62 and may even be slightly deeper. This ensures that upper compartment wall 70 firmly engages lower compartment wall 30 when cover 12 is closed against base 14. By closing cover 12 over base 14, primary lower compartment 13 and primary upper compartment 15 form a fully enclosed primary compartment; similarly, when cover 12 closes over base 14, the compartment walls 30, 70 engage and secondary lower compartment 31 and secondary upper compartment 51 form a fully enclosed secondary compartment. Two separate and distinct compartments are formed in the cassette, and the tissue sample within primary compartment 13 is physically isolated from the sample in the secondary compartment 31.

A seal 55 (e.g., rubber) may be placed on the lower compartment wall 30 in one embodiment to prevent leakage between upper compartment wall 70 and lower compartment wall 30 thereby ensuring that secondary compartment 31 will be sealed off completely from primary compartment 13 when cover 12 is closed over base 14. The seal 55 guarantees that the apparatus 10 will be divided into two separate and distinct compartments 13, 31.

Similar to the base 14, the cover 12 has a plurality of perforations 97B and 99B. First upper perforations 99B, located over the upper primary compartment 15, may be larger than the perforations 97B which are located over the upper secondary compartment 31. The upper perforations 97B, 99B serve the same purpose as the lower perforations 97A, 99A.

Figure 2:
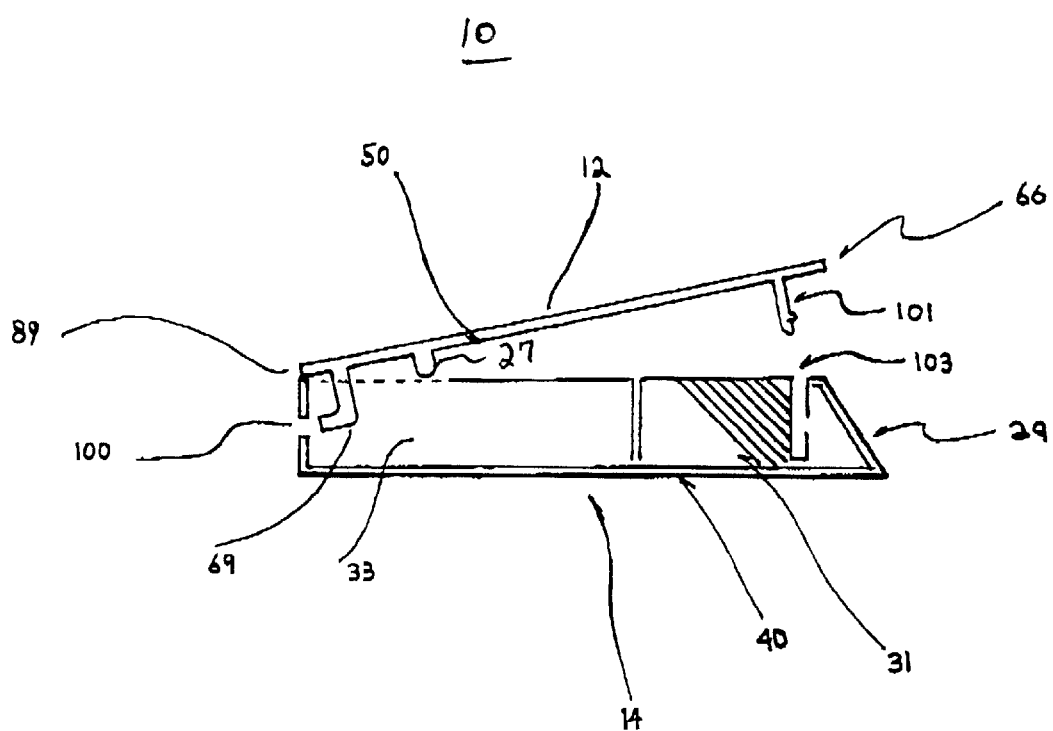
FIG. 2 is a cutaway view of the left side of the tissue cassette illustrated in FIG. 1.

Referring now to FIG. 2, a tab 69 having a generally L-shape depends from the rear of cover 12. A tab opening 100 is positioned on the base 14 and aligned with the tab 69. Furthermore, a latch 101 depends from the front of cover 12 and a corresponding latch opening 103 is positioned on the top surface 17 of the front endwall of the base 14. As the cover 12 is closed over base 14, the tab 69 is inserted into tab opening 100, latch 101 frictionally engages indent 103, ears 25, 27 receive and frictionally engage detents 35, 37, and the upper endwalls are received within and frictionally engage the lower endwalls; all of these elements act in concert to releasably secure the cover 12 to the base 14.

Referring again to FIG. 2, living hinge 89 is designed to break either upon mating the cover 12 against the base 14 or upon the first opening of the cover to retrieve the tissue samples inside. If the hinge 89 breaks during the mating operation, the interengagement of the endwalls, detents and tab 69 and latch 101 will releasably secure the cover 12 to the base 14 and resist undesirable separation.

As illustrated in FIGS. 1 and 2, slanted surface 29 projects outward from endwall 16 thereby providing a place to write indicia to identify the tissue sample(s). (The slanted surface 29 may be called the front of the apparatus 10.) For example, the name of the patient, doctor's name, dates and other designations may be written with a marker, grease pen or other appropriate means on the face of front surface 29.

A lip 66 may extend outward from base 50. After the tissue samples have been processed inside the cassette 10, applying upward pressure on lip 66 while holding base member 14 securely will release cover member 12 from base member 14, allowing access to the tissue sample inside.

In use, a tissue sample may be placed in secondary compartment 31, in primary compartment 13, or in both compartments. Usually, a relatively smaller tissue sample is secured in the primary compartment 13. The separate compartments ensure that both tissue samples are treated in an identical manner but are physically isolated from each other. Compared with prior art cassettes, the likelihood that small tissue samples will fall through the smaller perforations 97A, 97B of the secondary compartment is reduced. In addition, the likelihood that the relatively smaller tissue sample will get lost is decreased by placing it in secondary compartment 31 which is smaller than primary compartment 13.

Besides the various advantages in using a multi-compartment cassette wherein each compartment may have different sizes of perforations, the manufacturing process of the present cassette is substantially identical to prior art cassettes. No significant re-tooling of the dyes used to make prior cassettes are required.

Although this invention has been described and illustrated by reference to specific embodiments, it will be apparent to those skilled in the art that various changes and modifications may be made which clearly fall within the scope of this invention. The present invention is intended to be protected broadly within the spirit and scope of the appended claims.

I claim:

1. An apparatus for holding a biological specimen, the apparatus comprising:

a base having a perforated bottom member and a plurality of endwalls depending upward from the bottom member, said upward depending endwalls being joined to define a lower well, the base having a lower compartment wall depending upwards from the bottom member at a predetermined position to divide said lower well into at least two lower sections; and a cover that is movably attached to said base, said cover having a perforated top member and a plurality of endwalls depending downward from the top member, said downward depending endwalls being joined to define an upper well, the cover having an upper compartment wall depending downward from the top member, the position of the upper compartment wall being a mirror image of said lower compartment wall to divide said upper well into at least two upper sections corresponding to said two lower sections so that when the cover closes over the base one of said two lower sections and its corresponding one of said two upper sections form a primary compartment and the other of said two lower sections and its corresponding other of said two upper sections form a secondary compartment.

2. The apparatus of claim 1 wherein the perforations in said primary compartment are larger than the perforations in said secondary compartment.

3. The apparatus of claim 1 wherein the perforations in said primary compartment are different in shape than said perforations in said secondary compartment.

4. The apparatus of claim 1 wherein said cover is movably attached to said base via a living hinge along a common side.

5. The apparatus of claim 4 further comprising a tab that depends from the rear of the cover and a receptacle located on the rear of the base for receiving said tab, said tab and receptacle cooperating with each other to releasably secure the cover to the base.

6. The apparatus of claim 1 further comprising ears that depend downward from said downward depending endwalls of the cover and detents in said upward depending endwalls of the base aligned directly under said ears.

7. The apparatus of claim 1 further comprising a latch depending downward from the front of the cover and a latch receptacle in the front of the base for accepting said latch, said latch and latch receptacle working together to releasably join the cover to the bottom member.

8. The apparatus of claim 1 further comprising a plurality of lower compartment walls and a plurality of upper compartment walls for defining more than two compartments within the cassette.

9. A unitary two-compartment tissue cassette, the cassette comprising:

an open-topped perforated bottom member having lower endwalls and a lower compartment wall for defining two lower sections, each lower section adapted to receive a tissue sample; and a perforated cover member having upper endwalls and an upper compartment wall for defining two upper sections substantially identical in shape and position to their respective lower sections, the cover member adapted to cover the bottom member such that the first lower section and the first upper section form a primary compartment for securing a first tissue sample and contemporaneously the second lower section and the second upper section form a secondary compartment for securing a second tissue sample.

10. The cassette of claim 9 wherein the perforations in the primary compartment are of a different size than the perforations in the secondary compartment.

11. The cassette of claim 10 further comprising a latch depending downward from the front of the cover member and a latch receptacle proximate the front of the base member for accepting said latch, said latch and latch receptacle working together to releasably join the cover to the bottom member.

12. The cassette of claim 11 wherein said cover member depends from said base member via a living hinge along a common edge.

* * * * *